United States Patent [19]
Rosso

[11] Patent Number: 5,195,512
[45] Date of Patent: Mar. 23, 1993

[54] APPARATUS FOR EVACUATING EXCESS GASES FROM SURGERY PATIENT'S FACE

[76] Inventor: Sunny Rosso, 623 Redwood Ave., Corte Madera, Calif. 94925

[21] Appl. No.: 815,438

[22] Filed: Dec. 31, 1991

[51] Int. Cl.⁵ .................. A61M 16/00; A62B 9/04
[52] U.S. Cl. ..................... 128/200.24; 128/205.19; 128/910
[58] Field of Search ............... 128/200.24, 204.18, 128/205.19, 910

[56] References Cited

U.S. PATENT DOCUMENTS

| | | | |
|---|---|---|---|
| 3,859,993 | 1/1975 | Bitner | 128/200.24 X |
| 3,877,691 | 4/1975 | Foster. | |
| 3,990,112 | 11/1976 | Ciffolillo. | |
| 4,236,514 | 12/1980 | Moretti. | |
| 4,265,239 | 5/1981 | Fischer, Jr. et al. | |
| 4,321,917 | 3/1982 | Campbell | 128/200.24 X |
| 4,377,161 | 3/1983 | Whitt | 128/200.24 |
| 4,752,974 | 6/1988 | Haino. | |
| 4,770,169 | 9/1988 | Schmoegner. | |
| 4,865,049 | 9/1989 | Gatti. | |
| 4,895,172 | 1/1990 | Lindkvist. | |
| 4,998,529 | 3/1991 | Werjefelt. | |
| 5,012,805 | 5/1991 | Muckerheide. | |

FOREIGN PATENT DOCUMENTS 132848 11/1978 Fed. Rep. of Germany.
1516494 7/1978 United Kingdom.

OTHER PUBLICATIONS

Allen Medical Systems brochure, "Malleable Anesthesia Screen".
American Sterlizer Company brochure, "Surgical Equipment-2080 Table Accessories", May, 1974.

Primary Examiner—V. Millin
Assistant Examiner—Raleigh W. Chiu
Attorney, Agent, or Firm—Limbach & Limbach

[57] ABSTRACT

An apparatus for removing introduced or exhaled from the mouth and nose area of a patient via a suction device is disclosed. The apparatus includes a first flexible and hollow cylinder having one closed end and one open end and a plurality of small openings grouped together in a central portion of the first cylinder. The open end is attachable to the suction device. The second flexible and hollow cylinder is attachable to the operating table for supporting the first cylinder. A flexible tube extends through the second cylinder to provide rigidity and malleability to the second cylinder. The first cylinder is coupled to the second cylinder.

6 Claims, 2 Drawing Sheets

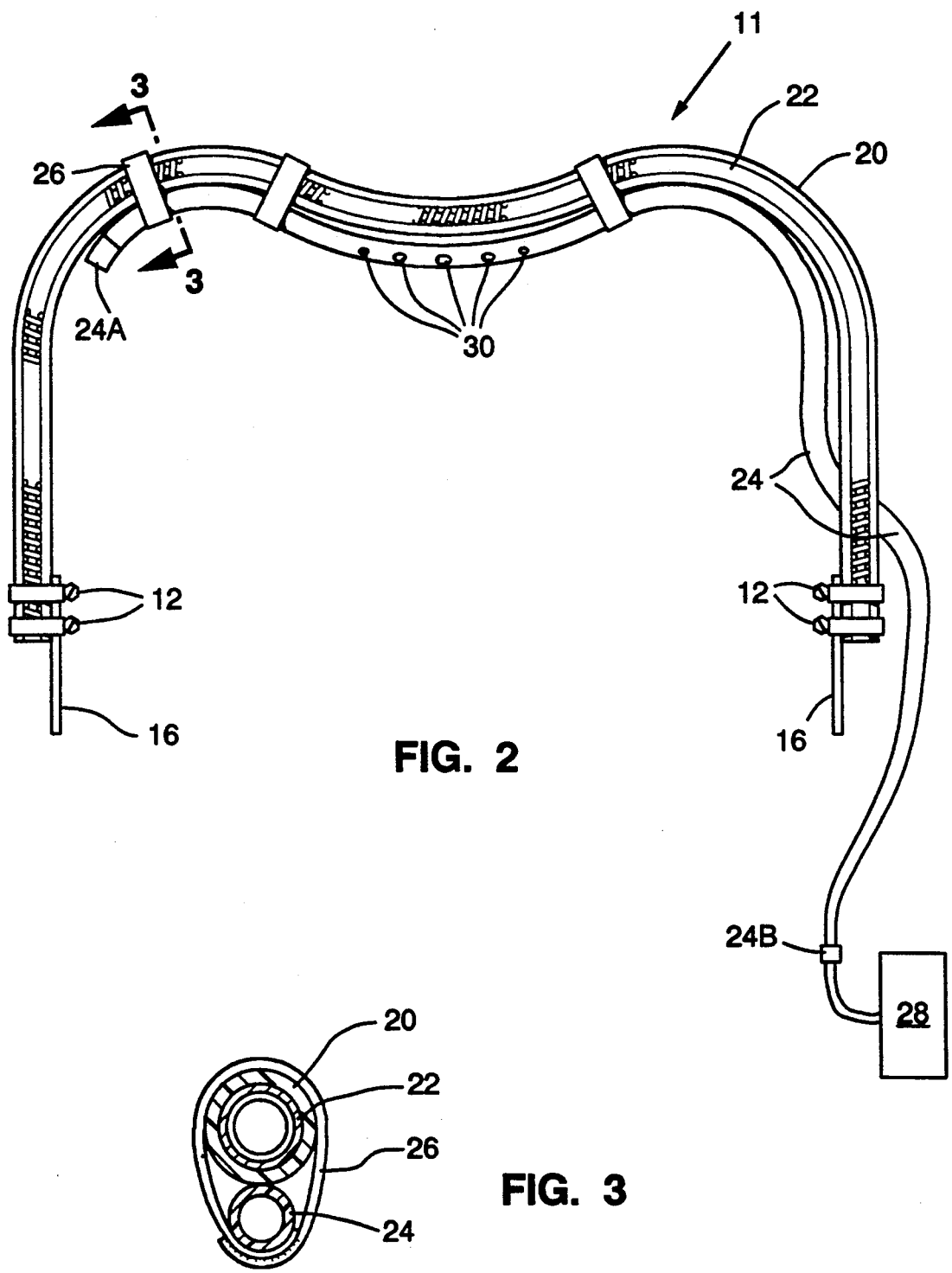

APPARATUS FOR EVACUATING EXCESS GASES FROM SURGERY PATIENT'S FACE

BACKGROUND

1. Field of the Invention

The present invention relates to gas removal devices, and more specifically, to an apparatus which will evacuate exhaled carbon dioxide and excess introduced oxygen from the face of a patient who is having surgery.

2. Discussion of the Prior Art

Many surgical procedures require that a patient lie supine on an operating table, possibly under the influence of anesthetics. In surgical procedures involving the face or head of the patient, an "operating tent" is constructed whereby surgical draping material is suspended over the head of the patient to prevent contamination of the operating site, while providing sufficient room for the surgeon to access the operating site. One of the problems inherent in using an operating tent is the build-up of carbon dioxide which has been exhaled by the patient in his breathing. Another problem is the potentially dangerous build-up of oxygen which has been introduced to the patient via nasal prongs or face mask. The most common method of removing these gases from the patient's face is the use of a mask to cover the nose and mouth area. As previously noted, such masks may also be used to deliver oxygen or other gases to the patient, as well as remove exhaled gases. Examples of such masks are disclosed in the following U.S. Pat. Nos.: 4,895,172; 5,012,805; 4,265,239; and 4,770,169. However, all of these face masks must have gas lines attached to them, and the gas lines, as well as the size of the mask, can restrict access by the surgeon to the patient's face for surgery. Another approach is disclosed in U.S. Pat. No. 4,865,049, in which a shield with a suction tube connected thereto extends across the chest of the patient for removing smoke which is created during electrocautery surgery. Similarly, U.S. Pat. No. 3,877,691 discloses a moveable panel having openings therein which can draw gases away from the face of a patient. However, the assembly is quite large and inflexible.

Thus, it would be desireable to have an apparatus that removes gases from the face area of a patient without restricting access to the patient, that is easily maneuvered to convenient positions, that supports draping materials away from the patient's face, thereby reducing potential claustrophobia in the patient, and that has disposable elements which can be easily replaced to prevent cross-contamination between patients.

SUMMARY OF THE INVENTION

The present invention is an apparatus for removing exhaled and excess gases from the mouth and nose area of a patient that is positioned for surgery on an operating table. Malleable support means are attached to the operating table in such a way as to extend across the chest or shoulder area of the patient. A first vinyl hose having one closed end and one open end is coupled to the support means. The open end of the first vinyl hose attaches to a suction device. The first vinyl hose also has a plurality of small openings grouped together in a central portion thereof. Preferably, the malleable support means comprises a second clear vinyl hose having a flexible brass tubing extending therethrough. The second vinyl hose and brass tubing are clamped at each end onto end plates which are coupled to the operating table.

A better understanding of the features and advantages of the present invention will be obtained by reference to the following detailed description of the invention and accompanying drawings which set forth an illustrative embodiment in which the principles of the invention are utilized.

BRIEF DESCRIPTION OF THE DRAWINGS

FIG. 2 is a front plan view of section of the gas removal device of the present invention.

FIG. 3 is a sectional plan view taken across section 3—3 of FIG. 2.

DETAILED DESCRIPTION OF THE INVENTION

Figure 1:
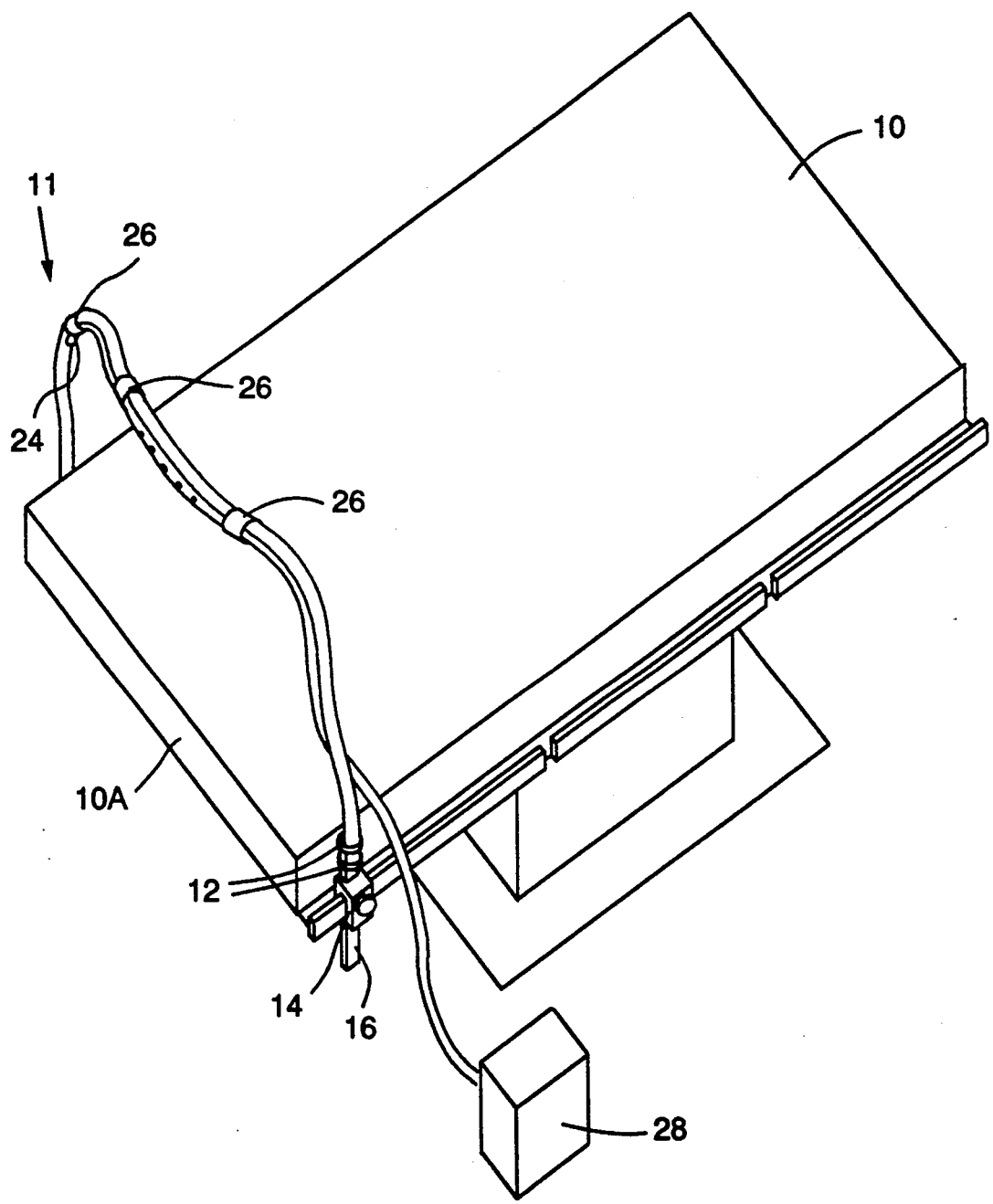
FIG. 1 is a perspective view of the present invention as mounted on an operating table.

Referring now to FIG. 1, an operating table 10 has a support apparatus 11 removably coupled thereto at bracket 14. Bracket 14 is a standard bracket of the type commonly used on the side rails of operating room tables to accomodate flat mounting posts. The support apparatus 11 is coupled near the head 10a of the table 10 so that it may be positioned proximate to the head of a patient who is lying supine on the table 10 during surgery. The support apparatus 11 is rigid yet malleable, so that it may be flexed to various positions while retaining its shape.

In the preferred embodiment, illustrated in FIGS. 2 and 3, the support apparatus 11 comprises a flexible clear vinyl hose 20 having a ⅜ inch outside diameter and a ⅝ inch inside diameter and ⅛ inch diameter flexible coated brass tubing 22 (such as that manufactured by Robert Manufacturing Company in Rancho Cucamonga, Ca.) running through the length of hose 20. The hose 20 and tubing 22 each have a length of 45 inches. The ends of hose 20 and tubing 22 are clamped onto metal end plates 16 by hose clamps 12. The end plates 15 are 5 inches in length by ⅝ inch wide by ⅛ inch thick. The total length of the support apparatus 11 is 51 inches. The hose clamps 12 and end plates 16 may be covered with shrinkwrap (not shown) to provided protection against sharp edges. The end plates 16 are removably mounted into brackets 14. The flexible brass tubing 22 provides sufficient rigidity to hold the hose 20 in any given position, yet it may be easily flexed to ny new position.

Another flexible clear vinyl hose 24 is coupled to the support apparatus 11, for example by VELCRO strips 26 in three locations, to provide quick and easy replacement of the hose 24, thereby eliminating the potential for cross-contamination between patients. The hose 24 has a ½ inch outside diameter and a 7/16 inch inside diameter and is 6 feet in length. One end 24a of the hose 24 is closed and the other end 24b of the hose 24 is open for connection to a standard vacuum suction device 28. A plurality of small openings 30 are grouped together in a central portion of the hose 24, such that the openings 30 will be proximate to the mouth and nose of the patient when the support apparatus 11 is flexed into position. Preferably, five graduated holes are provided, with the largest opening being approximately 3/16 inch diameter in the middle of the grouping, the next openings being 2/16 inch diameter, and the last openings being 1/16 inch diameter.

In operation, therefore, the hose 24 and support apparatus 11 are easily connected to a standard opening table 10 via end plates 16. The hose 24 and support apparatus 11 are then flexed into a position near the patient's mouth and nose during surgery. The support apparatus 11 is sturdy enough to elevate surgical draping material away from the patient's face thereby allowing visual and physical access to the patient by the anesthesiologist, the surgeon, or other person monitoring the status of the patient during surgery, as well as alleviating the potential for claustrophobia in the patient. Fore example, the support apparatus 11 elevates surgical draping material sufficiently to allow the use of a microscope during opthalmic procedures and head and neck surgery.

The hose 24 is connected to the suction device 28, and the suction drawing through openings 30 will evacuate any carbon dioxide which is exhaled by the patient during surgery and any excess build-up of introduced oxygen. Conveniently, the design of the present invention allows for efficient clean up between patients, as the hose 24 can be easily removed and replaced with a new hose, and the support apparatus 11 can be wiped down with standard operating room bactericidal and/or germicidal agents, thus preventing possible cross-contamination between patients.

It has been observed that the sound resulting from suction through the openings 30 (so-called "white noise") can also provide a pleasing diversion to the patient, and a patient may readily adopt a suggestion that the sound of the white noise can be likened to the sea, and this suggestion has been observed to provide an additional calming effect on the patient.

It should be understood that the invention is not intended to be limited by the specifics of the above-described embodiment, but rather defined by the accompanying claims.

I claim:

1. An apparatus for removing gases from the mouth and nose area of a patient via a suction device, wherein the patient is positioned for surgery on an operating table, comprising:
   a. a first cylinder which is flexible and hollow and has one closed end and one open end and a plurality of small openings grouped together in a central portion of the cylinder, said open end being attachable to the suction device;
   b. malleable support means attachable to the operating table for supporting the first cylinder;
   c. coupling means for coupling the first cylinder to the support means;
   d. movable support means further comprise a second cylinder which is flexible and hollow; and
   e. tubing means extending through the second cylinder for providing rigidity and malleability to the second cylinder.

2. An apparatus according to claim 1, further comprising bracket means for connecting the second cylinder and tubing means to the operating table.

3. An apparatus according to claim 2, wherein the bracket means comprises a pair of generally flat plates, and wherein the cylinder and tubing means are clamped onto the plates.

4. An apparatus according to claim 1, wherein the first cylinder is a first vinyl hose having an inside diameter of less than one-half inch, and wherein the second cylinder is a second vinyl hose having an inside diameter of less than one inch but more than one-half inch.

5. An apparatus according to claim 4, wherein the tubing means is flexible metal tubing.

6. An apparatus for removing gases from the mouth and nose area of a patient via a suction device, wherein the patient is positioned for surgery on an operating table, comprising:
   a. a first vinyl hose having one closed end and one open end and a plurality of small openings grouped together in a central portion of the first vinyl hose, said open end being attachable to the suction device;
   b. a second vinyl hose attachable to the operating table for supporting the first vinyl hose;
   c. a length of flexible brass tubing extending through the second vinyl hose; and
   d. coupling means for coupling the first vinyl hose to the second vinyl hose.

* * * * *